United States Patent
Öste et al.

(10) Patent No.: US 12,161,615 B2
(45) Date of Patent: Dec. 10, 2024

(54) FOOD SUPPLEMENT AND COMPOSITION FOR TREATING THE METABOLIC SYNDROME

(71) Applicant: DOUBLEGOOD AB, Lund (SE)

(72) Inventors: Rickard Öste, Lund (SE); Elin Östman, Kävlinge (SE); Inger Björck, Billinge (SE)

(73) Assignee: DOUBLEGOOD AB, Lund (SE)

( * ) Notice: Subject to any disclaimer, the term of this patent is extended or adjusted under 35 U.S.C. 154(b) by 0 days.

(21) Appl. No.: 18/213,059

(22) Filed: Jun. 22, 2023

(65) Prior Publication Data

US 2023/0414549 A1     Dec. 28, 2023

Related U.S. Application Data

(62) Division of application No. 15/775,778, filed as application No. PCT/EP2016/079019 on Nov. 28, 2016, now abandoned.

(51) Int. Cl.
*A61K 31/198*     (2006.01)
*A23L 33/16*     (2016.01)
(Continued)

(52) U.S. Cl.
CPC ............ *A61K 31/198* (2013.01); *A23L 33/16* (2016.08); *A23L 33/175* (2016.08); *A23L 33/18* (2016.08);
(Continued)

(58) Field of Classification Search
CPC ........ A23L 33/18; A23L 33/16; A23L 33/175; A61K 31/198; A61K 38/03; A61K 33/24; A61P 3/10; A23V 2002/00
(Continued)

(56) References Cited

U.S. PATENT DOCUMENTS 5,925,377 A     7/1999   Gerth et al.

FOREIGN PATENT DOCUMENTS

| CN | 1284297 A | 2/2001 |
| EP | 1680967 A1 | 7/2006 |

(Continued)

OTHER PUBLICATIONS

Mintel, "Apple Flavour Amino Acid Jelly Drink", XP002756069, retrieved from www.gnpd.com, Database accession No. 3569993, Aug. 21, 2015.

(Continued)

*Primary Examiner* — Subbalakshmi Prakash
(74) *Attorney, Agent, or Firm* — James S. Keddie; Bozicevic, Field & Francis LLP (57) ABSTRACT

The invention provides a food supplement comprising chromium and the five amino acids leucine, isoleucine, valine, threonine and lysine, wherein leucine, isoleucine, valine, threonine and lysine are the only amino acids present in the food supplement, and wherein the sum content of the five amino acids is from 1.75 to 3.5 g per dose of the food supplement, and wherein the content of chromium is from 4.5 to 61 μg per dose of the food supplement. A food composition comprising the food supplement, as well as the five amino acids for use in a method of treating, controlling or preventing diseases or conditions related to the metabolic syndrome, treating or controlling diabetes, treating, controlling or preventing obesity, promoting satiety, promoting weight loss, or promoting maintenance of a healthy bodyweight, by lowering postprandial glycaemia, and preferably also by lowering postprandial insulin secretion, are also provided.

11 Claims, 6 Drawing Sheets

(51) Int. Cl.
  *A23L 33/175* (2016.01)
  *A23L 33/18* (2016.01)
  *A61K 33/24* (2019.01)
  *A61K 38/03* (2006.01)
  *A61P 3/10* (2006.01)

(52) U.S. Cl.
  CPC .............. *A61K 33/24* (2013.01); *A61K 38/03* (2013.01); *A61P 3/10* (2018.01); *A23V 2002/00* (2013.01)

(58) Field of Classification Search
  USPC ............................................................ 426/2
  See application file for complete search history.

(56) References Cited

FOREIGN PATENT DOCUMENTS

| JP | 2005536215 A | 12/2005 |
| RU | 2012126178 A | 12/2013 |
| WO | WO 2004/017764 A1 | 3/2004 |
| WO | WO 2005/099483 A1 | 10/2005 |
| WO | WO 2007/049818 A1 | 5/2007 |
| WO | WO 2007/084059 A1 | 7/2007 |
| WO | WO 2012/177215 A1 | 12/2012 |

OTHER PUBLICATIONS

Ostman et al., "A drink containing amino acids and chromium picolinate improves postprandial glycemia at breakfast in healthy, overweight subjects", Functional Foods in Health and Disease, 2017, 7(2): 88-97.

Ostman et al., "A novel nutritional supplement containing amino acids and chromium decreases postprandial glucose response in a randomized, double-blind, placebo-controlled study", PLOS ONE, Jun. 24, 2020, 15(6): e0234237.

Nilsson et al., "Metabolic effects of amino acid mixtures and whey protein in healthy subjects: studies using glucose-equivalent drinks", Am J Nutr, 2007, 85: 996-1004.

Sahin et al., "The effects of whey protein and chromium picolinate supplementation on visceral fat and metabolic status in high-fat-fed rats", Mediterr J Nutr Metab, 2009, 2: 213-219.

Anderson, "Chromium and insulin resistance", Nutrition Research Reviews, 2003, 16: 267-275.

FOOD SUPPLEMENT AND COMPOSITION FOR TREATING THE METABOLIC SYNDROME

CROSS-REFERENCE TO RELATED APPLICATIONS

This application is a divisional of U.S. application Ser. No. 15/775,778, filed on May 11, 2018, which is a § 371 national phase of International Application No. PCT/EP2016/079019, filed on Nov. 28, 2016, which claims the benefit of European Patent Application No. 15196852.6, filed on Nov. 27, 2015, which applications are incorporated by reference herein.

FIELD OF THE INVENTION

The present invention relates to the field of food supplements suitable for treating the metabolic syndrome. In particular the present invention relates to a food supplement comprising chromium and the amino acids leucine, isoleucine, valine, threonine and lysine, a food composition comprising the food supplement, and the amino acids leucine, isoleucine, valine, threonine and lysine for use in a method of treating the metabolic syndrome.

BACKGROUND OF THE INVENTION

The metabolic syndrome (MetS) is a cluster of metabolic disorders, including elevated blood pressure, hyperglycaemia, dyslipidaemia and obesity, which increases the risk of cardiovascular disease (CVD) and type 2 diabetes mellitus (T2DM). Evidence is at hand suggesting that lowering of postprandial hyperglycaemia constitutes an important preventive measure to reduce the incidence of CVD in diabetic patients. It has further been shown that the 2-hour postprandial blood glucose concentration is a better predictor of future CVD risk than fasting glucose levels. Also the 1-hour postprandial blood glucose has been shown to predict CVD risk emphasising the cardio-preventive benefits of a tight post-prandial glycaemic control in T2DM. In recent years, sub-clinical inflammation has emerged as an important component in the aetiology of the MetS, T2DM and CVD. Of interest in this respect is that hyper-glycaemia may trigger release of inflammatory markers and oscillatory hyperglycaemia has been shown to promote higher inflammation than does chronic hyperglycaemia, indicative of a relation between elevated postprandial glycaemic levels and sub-clinical inflammation. The preventive potential of tight postprandial glycaemic control is also evident from interventions with Acarbose, an alpha-glucosidase inhibitor known to lower postprandial glycaemia. Consequently, Acarbose treatment markedly lowered the risk of diabetes in subjects with impaired glucose tolerance (IGT). Evidence from several large prospective cohort studies also suggests that lowering of postprandial blood glucose may have a greater role in preventing T2DM and CVD if implemented early in the course of disease development, or even before onset. Hence, improved management of postprandial hyperglycaemia could be beneficial both in patients with T2DM and IGT, as well as in primary prevention with respect to the general population.

WO200784059 describes a protein composition comprising an amino acid mixture comprising leucine, isoleucine, valine, lysine and threonine in an amount from about 35 to about 90 g/100 g of the total amount of the amino acid part. The composition is useful for control of blood glucose levels in a mammal. However, the amino acids themselves, by being insulin secretagogues, cause an increased postprandial insulin secretion.

WO2012177215 discloses a food supplement comprising the five amino acids leucine, isoleucine, valine, threonine and lysine, and the mineral chromium, which food supplement significantly reduces post-prandial glycaemia, while also limiting postprandial insulin secretion.

WO2005099483 discloses an ingestible composition containing carbohydrates, fats, proteins (including a plethora of different amino acids), vitamins and minerals wherein relative amounts of the components of the composition are chosen such that an intake of said product allegedly reduces the effects of metabolic syndrome.

EP1680967 discloses a food supplement comprising milk proteins and inter alia tyrosine.

WO2007049818 discloses a composition comprising different amounts of lysine, threonine, leucine, isoleucine, and valine.

Despite the recent advancements there is still a need for further means and methods for treating the metabolic syndrome.

Accordingly it is an object of the present invention to provide a food supplement and food composition capable of treating the metabolic syndrome.

It is a further object of the present invention to provide a food supplement and food composition capable of reducing postprandial glycaemia.

It is yet a further object of the present invention to provide a food supplement and food composition capable of reducing postprandial glycaemia while reducing postprandial insulin secretion.

It is yet a further object of the present invention to provide a food supplement and food composition having lower energy content and/or a better, or less, taste.

It is yet a further object of the present invention to provide a method for treating the metabolic syndrome.

SUMMARY OF THE INVENTION

At least one of the above objects, or at least one of the objects which will be evident from the below description, is according to a first aspect of the invention achieved by a food supplement comprising the five amino acids leucine, isoleucine, valine, threonine and lysine, wherein the sum content of the five amino acids is less than 6.9 g, namely wherein leucine, isoleucine, valine, threonine and lysine are the only amino acids present in the food supplement, and wherein the sum content of the five amino acids is from 1.75 to 3.5 g per dose of the food supplement, and wherein the content of chromium is from 4.5 to 61 µg per dose of the food supplement.

Thus the present invention is based on the unexpected finding that a lower amount of the five amino acids, i.e. from 1.75 to 3.5 g as will be further evidenced in the examples, actually reduces postprandial glycaemia by the same amount, or even reduces it further, than the higher amounts of the same five amino acids disclosed in the prior art. Further this lower amount of the five amino acids also reduces the postprandial insulin secretion, as will be further evidenced in the examples, thereby providing better insulin economy and hence reducing the systemic effects of insulin secreted postprandially. These lower amounts of the five amino acids also reduces the calorie content of the food supplement, and reduces the taste of the food supplement, thus providing a food supplement which is easily acceptable for the consumer of the food supplement, also when the food supplement is used for prevention or treatment of the metabolic syndrome.

Accordingly the food supplement according to the first aspect of invention, when consumed prior to or at the same time as a meal, prevents postprandial glycaemia and thereby prevents or delays the progression of the metabolic syndrome. Furthermore, the reduced postprandial insulin secretion obtained by the consumption of the food supplement according to the first aspect of the present invention prevents or delays the progression of Insulin Resistance.

At least one of the above objects, or at least one of the objects which will be evident from the below description, is according to a second aspect of the invention further achieved by a food composition comprising the food supplement according to the first aspect of the present invention, wherein the five amino acids leucine, isoleucine, valine, threonine and lysine are the only amino acids in the food composition that are free or provided as peptides comprising at the most 10 amino acids. The food composition may consist essentially of the food supplement according to the first aspect of the present invention and water.

The food composition may preferably be provided as beverage, such as water, e.g. a table water, and may therefore serve as a drink to be taken with a meal.

At least one of the above objects, or at least one of the objects which will be evident from the below description, is according to corresponding third and fourth aspects of the present invention achieved by the five amino acids leucine, isoleucine, valine, threonine and lysine, for use in a method of treating, controlling or preventing diseases or conditions related to the metabolic syndrome, treating or controlling diabetes, treating, controlling or preventing obesity, promoting satiety, promoting weight loss, or promoting maintenance of a healthy bodyweight, wherein 1.75 to 3.5 g of the five amino acids is administered to, or consumed by, a subject prior to, or at the same time as, the subject consumes a meal, and wherein chromium, in an amount of 4.5 to 61 µg, is also administered to, or consumed by, the subject prior to, or at the same time as the subject consumes a meal, and, a method of treating, controlling or preventing diseases or conditions related to the metabolic syndrome, treating or controlling diabetes, treating, controlling or preventing obesity, promoting satiety, promoting weight loss, or promoting maintenance of bodyweight, wherein 1.75 to 3.5 g of the five amino acids leucine, isoleucine, valine, threonine and lysine is administered to, or consumed by, a subject prior to, or at the same time as, the subject consumes a meal, and wherein chromium, in an amount of 4.5 to 61 µg, is also administered to, or consumed by, the subject prior to, or at the same time as the subject consumes a meal, respectively.

Definitions

In the context of the present application and invention the following definitions apply: The term "food supplement" refers to an ingestible (consumable or drinkable) composition which affects the response of the body (mammal, e g human or animal) to a food. The food supplement may be added to a food before, during or after preparation of the food. The food supplement may also however be ingested on its own, preferably before or during a meal, or in between meals.

The term "food composition" refers to a food, i.e. an ingestible (consumable or drinkable) composition.

The term "probiotic bacteria" is intended to mean any micro-organism which after administration exercise health beneficial effects, within the mammal it is administrated to.

The term "Insulin Resistance Syndrome" (IRS) is used interchangeably with the term "Metabolic syndrome" (MetS) and refers to a cluster of dysfunctions and metabolic risk factors which identifies individuals with increased risk of type-2 diabetes and cardiovascular disease. IRS or MetS may be characterized by at least two of the following abnormalities: insulin resistance, hyperinsulinemia, impaired glucose tolerance, hyperlipidemia, hypercholesterolemia, hypertension, and abdominal obesity The term "Insulin resistance" (IR) refers to a condition with impairment of insulin receptor signalling and a condition of impaired ability for glucose regulation.

The term "Insulin sensitivity" refers to a measure of degree of insulin action, with an insulin sensitive condition corresponding to a normal insulin receptor signalling and normal glucose metabolism.

The term "Impaired glucose tolerance (IGT)" refers to a pre-diabetic condition which is characterized by lowered insulin sensitivity in the fasting state, and/or post-prandial blood glucose responses above normal following a glucose challenge.

The term "Hyperinsulinemia" refers to a condition with elevated insulin levels.

The term "GI" refers to Glycaemic Index, that is the post-prandial glycaemic response (incremental glycaemic area under curve) to a carbohydrate test product expressed as a percentage of the corresponding response (incremental glycaemic area under curve) with a carbohydrate equivalent amount of a reference product or pure glucose taken by the same subject. In the literature GI refers to a time period up to 1.5 or 2 hours post meal.

The term "Glycaemic profile", GP, is defined as the duration (min) for the incremental post-prandial glycaemic response divided by the incremental glucose peak (min/mM) elicited by a food. GP may be a better predictor of acute postprandial insulin demand, subjective rating of satiety, and of second meal voluntary food intake compared to GI (see Rosen et al, Nutrition Journal 2009).

In the context of the present invention "treating" refers to mitigating either a pre-existing disease state, acute or chronic, or a recurring condition.

In the context of the present invention "controlling" refers to preventing further deterioration of a pre-existing disease state, acute or chronic, or a recurring condition, or lessening or limiting the symptoms or effects of a pre-existing disease state, acute or chronic, or a recurring condition.

In the context of the present invention "preventing" is to be understood as encompassing lessening the risk or likelihood of the emergence or diagnosis of a disease state.

BRIEF DESCRIPTION OF THE FIGURES

The invention will now be described in further detail with reference to the figures in which.

DETAILED DESCRIPTION

The first aspect of the present invention relates to a food supplement comprising chromium and the five amino acids leucine, isoleucine, valine, threonine and lysine, wherein leucine, isoleucine, valine, threonine and lysine are the only amino acids present in the food supplement, and wherein the sum content of the five amino acids is from 1.75 to 3.5 g per dose of the food supplement, and wherein the content of chromium is from 4.5 to 61 µg per dose of the food supplement. As was shown earlier in WO200784059, these five amino acids reduce postprandial glycaemia. Tables 3, 5 and 7 now show that the food supplement according to the first aspect of the present invention, when included in a food composition in the form of a table water consumed at least partly prior to a meal, reduces postprandial glycaemia and postprandial insulin secretion. Postprandial glycaemia is reduced significantly, when compared to the reference meal without the food supplement, without significantly increasing the postprandial insulin secretion compared to the reference meal as is the case for the prior art food supplements containing 6.9 g or more of the amino acids.

The reduction of postprandial insulin secretion is complete, i.e. the postprandial insulin secretion is approximately the same as for the reference meal, for the lower amounts 3.5 g and 1.75 g of the amino acids, i.e. between 1.75 g and 3.5 g, such as 2.6 g. The lowered postprandial insulin secretion reduces systemic effects of insulin and prevents insulin resistance, and the lower amounts of the amino acids in the food supplement according to the first aspect of the present invention also reduces the calorie content of the food supplement, and reduces the taste of the food composition. This provides a food supplement which is easily acceptable for the consumer of the food supplement, also when the food supplement is used for prevention treatment of the metabolic syndrome, or even when the food supplement is used by the general healthy public wishing to regulate their blood glucose levels after a meal.

Accordingly it may, surprisingly, be concluded that the lower amounts of the five amino acids provide an overall better treatment, controlling or prevention of conditions associated with the metabolic syndrome.

The food supplement may alternatively be defined as a food supplement comprising amino acids and at least one mineral wherein a) the amino acid content consists of leucine, isoleucine, valine, threonine, lysine, and b) the mineral content comprises at least chromium, and wherein the sum content of the amino acid content is from 1.75 to 3.5 g per dose of the food supplement, and wherein the content of chromium is from 4.5 to 61 µg per dose of the food supplement.

Any reference to the five amino acids is to be understood as referring to leucine, isoleucine, valine, threonine and lysine.

The amino acids may each independently be present in amounts from 1 to 99%, such as 1-80%, from 10-50, 10-40, 10-35, 10-25%, such as from 6-12%, 7-15%, from 5-35%, 40-60%, 50-75%, 46-37%, 3-16%, such that the sum of all present amino acids is 100%. In one embodiment, leucine is present in from 1 to 99%, such as from 1 to 80%, such as from 10 to 40%, such as from 10-50, 10-40, 10-35, 10-25%, such as from 6-12%, 7-15%, from 5-35%, 40-60%, 50-75%, 46-37%, 3-16%, or such as 25-29%, such as 25%, 26%, 27%, 28%, 29%.

In one embodiment, isoleucine is present in from 1 to 99%, such as from 1 to 80%, such as from 10 to 40%, such as from 10-50, 10-40, 10-35, 10-25%, such as from 6-12%, 7-15%, from 5-35%, 40-60%, 50-75%, 46-37%, 3-16%, or such as 11-14%, such as 9%, 10%, 11%, 12%, 13%, 14%.

In one embodiment, valine is present in from 1 to 99%, such as from 1 to 80%, such as from 10 to 40%, such as from 10-50, 10-40, 10-35, 10-25%, such as from 6-12%, 7-15%, from 5-35%, 40-60%, 50-75%, 46-37%, 3-16%, or such as 11-14%, such as 13%.

In one embodiment, threonine is present in from 1 to 99%, such as from 1 to 80%, such as from 10 to 40%, such as from 10-50, 10-40, 10-35, 10-25%, such as from 6-12%, 7-15%, from 5-35%, 40-60%, 50-75%, 46-37%, 3-16%, or such as 25-29%, such as 25%, 26%, 27%, 28%, 29%.

In one embodiment, lysine is present in from 1 to 99%, such as from 1 to 80%, such as from 10 to 40%, such as from 10-50, 10-40, 10-35, 10-25%, such as from 6-12%, 7-15%, from 5-35%, 40-60%, 50-75%, 46-37%, 3-16%, or such as 18-29%, such as 18%, 19%, 20%, 21%, 22%, 23%, 24%, 25%, 26%, 27%, 28%, 29%.

The sum percentages of all present amino acids should be 100%.

The rate at which the amino acids are released during digestion and absorbed into the circulation is affected by the form in which the amino acids are present Amino acids present in a form which is soluble, rapidly digested and/or easily absorbed enhances the plasma concentration of amino acids and promotes insulin secretion. Thus the five amino acids may be present in a form selected from the group of: peptides consisting of one or more of the amino acids, free amino acids, or a mixture thereof. The peptides may consist of 2, 3, 4, 5 or 6 amino acids, or more, for example up to 10 amino acids or up to 20 amino acids, selected from the group of leucine, isoleucine, valine, threonine and lysine. The peptides need not be identical to each other. Instead the mixture containing peptides may differ in for example amino acid sequence and/or length. Also from taste point of view it may be suitable for certain amino acids to be present as part of a peptide.

Preferably the five amino acids are present as free amino acids or as peptides with up to amino acids.

One or more of the five amino acids or peptides may be synthesized or may be derived from for example one or more of the sources selected from the group comprising whey, soy-, casein-, oat-, egg-, blood-, pea-, barley-, fish protein, gelatine and α-lactalbumin. If one or more of the five amino acids are derived from whey, the whey may be obtained from any mammal source such as from cows, goats. If one or more of the five amino acids are obtained from a plant material such as soy, they may be obtained from for example genetically modified cultivars, such as by having an increased content of one or more of the amino acids.

In some embodiments of the food supplement according to the first aspect of the present invention the food supplement further comprises one or more of flavouring agents, aromas (examples of ingredients giving taste) (such as orange, lemon, bergamot, grapefruit, banana, apricot and strawberry), colours, fillers, preservatives, sweeteners, gel forming agents, binders, lubricants, emulsifiers, vitamins, effervescent agents such as citric acid, tartaric acid, malic acid, fumaric acid, adipic acid, acid citrates, succinic acid, sodium carbonate, potassium carbonate, sodium bicarbonate, potassium bicarbonate, calcium bicarbonate, magnesium carbonate, sodium glycocarbonate, and carboxylysine, and mixtures thereof.

The food supplement according to the first aspect of the present invention may in particular further comprise one or more minerals such as calcium and/or magnesium. Magnesium may be present in amounts of for example 600 mg/serving, such as 100-600 mg. Calcium may be present in amounts such as for example 200, 300, 400, 400-1200, 500-1300 mg. Magnesium may be present in amounts of for example from 10 to 100 mg, such as for example 10 to 70 mg, 10 to 50 mg, 10 to 40 mg, 10 to 23 mg, or for example from 15 to 60 mg, or 15 to 35 mg. For example, Magnesium may be present in amounts of for example, 15, 20, 23, 40, 50, 65, 70, 80, 85, or 90 mg.

Calcium may be present in amounts of for example from 25 to 250 mg, such as for example 25 to 220, 30 to 200, 30 to 170, 30 to 150, 30 to 120, 30 to 100, 30 to 70, 30 to 50 mg, or for example 25 to 75, 25 to 65, 25 to 45 mg.

The food supplement according to the first aspect of the present invention may in particular further comprise acids such as ascorbic acid (Vitamin C). Vitamin C may be present in amounts of for example 0.5 g, 1 g, 1.5 g, 2 g, 2.5 g or 3 g. The food supplement may in particular further comprise antioxidants such as Vitamin C.

In further embodiments the food supplement according to the first aspect of the present invention such as yeasts such as *Saccharomyces, Debaromyces, Candida, Pichia* and *Torulopsis*, moulds such as *Aspergillus, Rhizopus, Mucor*, and *Penicillium* and *Torulopsis* and bacteria such as the genera *Bifidobacterium, Bacteroides, Clostridium, Fusobacterium, Melissococcus, Propionibacterium, Streptococcus, Enterococcus, Lactococcus, Staphylococcus, Peptostreptococcus, Bacillus, Pediococcus, Micrococcus, Leuconostoc, Weissella, Aerococcus, Oenococcus* and *Lactobacillus*. Specific examples of probiotic microorganisms are: *Saccharomyces cereviseae, Bacillus coagulans, Bacillus licheniformis, Bacillus subtilis, Bifidobacterium bifidum, Bifidobacterium infantis, Bifidobacterium longum, Enterococcus faecium, Enterococcus faecalis, Lactobacillus acidophilus, Lactobacillus alimentarius, Lactobacillus casei* subsp. *casei, Lactobacillus casei* Shirota, *Lactobacillus curvatus, Lactobacillus delbruckii* subsp. *lactis, Lactobacillus farciminus, Lactobacillus gasseri, Lactobacillus helveticus, Lactobacillus johnsonii, Lactobacillus reuteri, Lactobacillus rhamnosus (Lactobacillus GG), Lactobacillus sake, Lactococcus lactis, Micrococcus varians, Pediococcus acidilactici, Pediococcus pentosaceus, Pediococcus acidilactici, Pediococcus halophilus, Streptococcus faecalis, Streptococcus thermophilus, Staphylococcus carnosus, Staphylococcus xylosus, Lactobacillus acidophilus, Lactobacillus thermofilus, Lactobacillus bulgaricus, Lactobacillus plantarum, Lactobacillus reuteri, Bifidobacterium bifidum, Bifidobacterium longum. Caseii, Lactobacillus iners*. For example, the probiotic microorganism may be selected from the group consisting of *Lactobacillus acidophilus, Lactobacillus thermophilus, Lactobacillus bulgaricus, Lactobacillus plantarum, Lactobacillus reuteri, Bifidobacterium bifidum, Bifidobacterium longum. Caseii* and *Lactobacillus iners*.

The probiotic microorganisms may be in powdered, dried form; especially in spore form for microorganisms which form spores. Further, if desired, the probiotic microorganism may be encapsulated to further increase the probability of survival; for example in a sugar matrix, fat matrix or polysaccharide matrix.

In the context of the present invention the term per dose encompasses the term per serving.

In the food supplement according to the first aspect of the present invention the sum content of the five amino acids is from 1.75 to 3.5 g.

This range of sum contents correspond to the lower and middle amount of the five amino acids tested in the examples. As described above a sum content of the five amino acids from 1.75 g to 3.5 g, as shown in table 3 and 5, provides a significant reduction of postprandial glycaemia and an essentially complete reduction of the postprandial insulin secretion, thus providing the benefits of the five amino acids in regard of lowering postprandial glycaemia, without at the same time increasing the postprandial insulin secretion.

In alternative embodiments of the food supplement according to the first aspect of the present invention the sum content of the five amino acids is from 1.75 to 2.6 g, or from 2.6 to 3.5 g, per dose of the food supplement.

In the preferred embodiment of the food supplement according to the first aspect of the present invention the content of chromium is from 4.5 to 31.1 µg, such as 15.5 to 31.1 µg, per dose of the food supplement.

This corresponds to from 36 to 250 µg, such as from 125 to 250 µg CrPic (Chromium(III) Picolinate).

In one embodiment of the food supplement to the first aspect of the present invention leucine is present in an amount of 10-50%, isoleucine is present in an amount of %, valine is present in an amount of 10-25%, threonine is present in an amount of % and lysine is present in an amount of 10-25%, wherein the percentages are calculated on the sum content of the five amino acids in the food supplement and wherein the sum of the percentages of the five amino acids in the food supplement is 100%.

As the sum of the percentages of the five amino acids should be 100% the percentage of each amino acid should be selected, within the specified range, so that the total is 100%.

In the food supplement to the first aspect of the present invention leucine, isoleucine, valine, threonine and lysine are the only amino acids present in the food supplement. No further amino acids are necessary to obtain the reduction in postprandial glycaemia. In other words there are no other amino acids than these five in the food supplement. This may also be stated as the amino acid content of the food supplement consisting of leucine, isoleucine, valine, threonine and lysine.

In one embodiment of the food supplement to the first aspect of the present invention the food supplement consists essentially of chromium and the five amino acids leucine, isoleucine, valine, threonine and lysine.

The term "consists essentially of" means that only those further components which do not materially affect the basic and novel characteristic of the food supplement may be included in this embodiment. Components such as flavouring agents, aromas (examples of ingredients giving taste)

(such as orange, lemon, bergamot, grapefruit, banana, apricot and strawberry), colours, fillers, preservatives, sweeteners (excluding sweeteners comprising amino acids and/or carbohydrates), gel forming agents, binders, lubricants, emulsifiers, vitamins, effervescent agents such as citric acid, tartaric acid, malic acid, fumaric acid, adipic acid, acid citrates, succinic acid, sodium carbonate, potassium carbonate, sodium bicarbonate, potassium bicarbonate, calcium bicarbonate, magnesium carbonate, sodium glycocarbonate, and carboxylysine, and mixtures thereof, are considered components which do not affect the function or the effect of the food supplement.

The food supplement according to the first aspect of the present invention the food supplement comprises chromium.

As shown in example 1 and as shown by WO2012177215, chromium plays a role in limiting postprandial glycaemia and insulin secretion.

The chromium may be present in any form which is suitable for consumption such as for example one or more of chromium picolinate, chromium nicotinate, chromium polynicotinate, chromium propionate, chromium acetylacetonate, chromium-citrate, chromium nicotinate, chromium-dinicocysteinate, Niacin-bound chromium, Amino acid chelates with chromium, chromium chelavite, or combinations thereof.

In one embodiment, chromium is present as Chromium picolinate, such as chromium tripicolinate, chromium dipicolinate, chromium monopicolinate or combinations thereof. In a further embodiment, chromium is present as Chromium tripicolinate. In another embodiment, chromium is present as Chromium dinicocysteinate (CDNC). CDNC and chromium picolinate have both shown positive effects on different metabolic markers for longer term glucose regulation.

The percentage of chromium in chromium tripicolinate (i.e. chromium (III) picolinate) is 12.43%, meaning that 1000 micrograms Chromium(III) Picolinate contains 125 micrograms Chromium. Sometimes this is expressed as 100 micrograms Chromium(III) picolinate equals 19.2 micromoles Chromium, i.e. 12.4 micrograms Chromium.

In the food supplement according to the first aspect of the present invention the content of chromium is between 4.5 µg and 61 µg.

The relationship between chromium and the sum content of the five amino acids leucine, isoleucine, valine, threonine and lysine in the food supplement may be for example between 4 and 10 microgram chromium per g sum content of the amino acids. Further examples include 4-9 micrograms, 5-10 micrograms, 6-10 micrograms, 5-10 micrograms, and 5-9 micrograms chromium per g sum content of the amino acids. Further examples are 1, 2, 3, 4, 5, 6, 7, 8, 9, 10 microgram chromium per g sum content of the amino acids.

In this embodiment 4.5 µg chromium corresponds to the amount of chromium in 100 ml of the table water, i.e. food composition, comprising the food supplement with the lowest (1.75 g in total) amount of the five amino acids, see table 1 and the 1.1. Materials and Methods section of the examples.

In the preferred embodiment of the food supplement according to the first aspect of the present invention the content of chromium is from 4.5 to 31.1 µg, such as 15.5 to 31.1 µg, per dose of the food supplement.

This corresponds to from 36 to 250 µg, such as from 125 to 250 µg CrPic (Cromium (III) Picolinate)

In further embodiments of the food supplement according to the first aspect of the present invention the food supplement is in the form selected from the group consisting of liquid concentrates, effervescent forms, powders and granulates.

The liquid concentrates may comprise the five amino acids, and chromium and other components if present, in a liquid such as water or oil. In the context of the present invention a liquid concentrate is to be understood as encompassing a gel. The gel may for example be formed by adding a gel forming agent to a liquid concentrate.

The liquid concentrates may be consumed directly or mixed with for example water or other beverage. The liquid concentrates may for example be packaged in a bottle or flexible pouch.

Effervescence is the reaction (in water) of acids and bases producing carbon dioxide. Examples of acids used in this reaction are citric acid, tartaric acid, malic acid, fumaric acid, adipic acid, acid citrates, succinic acid and mixtures thereof. Citric acid is the most commonly used, and it imparts a citrus-like taste to the product. Examples of bases used in the effervescent reaction are sodium carbonate, potassium carbonate, sodium bicarbonate, potassium bicarbonate, calcium bicarbonate, magnesium carbonate, sodium glycocarbonate, carboxylysine and mixtures thereof. Sodium bicarbonate is very common in effervescent formulas.

The effervescent form may for example comprise an effervescent tablet or an effervescent powder or an effervescent granulate. The effervescent tablet, powder and granulate may be packaged in a pouch or other container and added to an aqueous liquid such as water to obtain a drink comprising the food supplement according to the first aspect of the present invention The powders may additionally be pressed into tables or granulates. The granulates may be provided in a capsule to be consumed whole or opened to sprinkle the granulates on a food or in a liquid.

In one embodiment of the food supplement according to the first aspect of the present invention the sum content of the five amino acids is 2.6 g per dose of the food supplement. In this embodiment the content of chromium may be 31.1 µg (corresponding to 250 µg CrPic) per dose.

In another embodiment of the food supplement according to the first aspect of the present invention the sum content of the five amino acids is 1.75 g per dose of the food supplement. In this embodiment the content of chromium may be 15.5 µg (corresponding to 125 µg CrPic) per dose.

In another embodiment of the food supplement according to the first aspect of the present invention the sum content of the five amino acids is 3.5 g per dose. In this embodiment the content of chromium may be 31.1 (corresponding to 250 µg CrPic) per dose.

The food supplement according to the first aspect of the present invention may be used for producing a food composition comprising the food supplement.

The second aspect of the present invention relates to a food composition comprising the food supplement according to the first aspect of the present invention, wherein the five amino acids leucine, isoleucine, valine, threonine and lysine are the only amino acids in the food composition that are free or provided as peptides comprising, or consisting of, at the most 10 amino acids.

The food composition may comprise a functional food, functional feed, nutraceutical, nutritional supplement, medicament and pharmaceutical comprising the food supplement.

The food composition may appear as a solid, a semi-solid such as a cream or paste, a gel, a liquid, a dispersion, a suspension or an emulsion, a powder for dissolution, or in any desired form. The composition may appear, for example, in the form of any kind of food, feed, drink, functional food and functional feed, e.g. as a cereal product such as flakes, bars, breads, cookies and biscuits, as juice, jam, spread, soft drink, oat suspension, soya milk, meat product, dairy products such as yoghurt, chocolate, cheese, pudding and other dairy desserts, spreadable products, frozen desserts and ice-cream, malt drink, coffee, tea, sport drink, meal replacement, gruel, porridge, ready to eat meals, infant formula, baby food; in the form of a pharmaceutical composition and medicament, e.g. as a powder, an aggregate, a granulate, a tablet, a coated tablet, a lozenge, a capsule, a drink, a syrup, a composition for tube feeding, for enteral intake, for oral administration and for enteral administration.

The effects of the food supplement, i.e. the reduction of postprandial glycaemia and preferably the reduction of postprandial insulin secretion and/or the increase of postprandial GLP-1 levels, are maintained even when the food composition, in addition to the food supplement, comprises proteins. This is because the five amino acids in the food supplement are taken up by the body faster than proteins. This effect is maintained both when the five amino acids are free and in peptides up to 10 amino acids.

Preferably however the five amino acids are present as free amino acids or dipeptides.

In the preferred embodiment of the food composition according to the second aspect of the present invention the food composition is in an amount suitable for being consumed prior to, or together with, a meal.

This is advantageous as the food composition may then be used to lower postprandial glycaemia after conventional meals, i.e. the food composition according to the second aspect of the present invention need not replace conventional meals, instead consumers may continue consuming their conventional or usual meals yet receive the benefit of lowered postprandial glycaemia when the food composition is consumed prior to or together with the meal conventional or usual meal.

The meal may for example be breakfast, brunch, lunch, a snack, dinner, supper, and evening meal. The meal typically contains carbohydrates or sugars.

In the preferred embodiment of the food composition according to the second aspect of the present invention the amount of the food composition is from 5 ml to 1000 ml, such as from 100 ml to 500 ml, such as from 200 ml to 330 ml, or alternatively from 5 g to 1000 g, such as from 100 g to 500 g, such as from 200 ml to 330 ml.

The amount of the food composition typically depends on the form of the food composition where liquid food composition generally may be in larger volumes/amounts and solid food compositions generally are in smaller volumes/amounts.

In the preferred embodiment of the food composition according to the second aspect of the present invention the food composition is a beverage such as water, tea, malt beverages, coffee, soft drinks, juice, yoghurt, milk, soymilk or oatmilk.

This is advantageous as beverages are easily consumed together with meals and as the five amino acids in a food composition in the form of a beverage are quickly taken up by the body of the consumer of the food beverage.

It is especially advantageous when the beverage is tea, malt beverages, coffee, soft drinks, or juice because these beverages have taste profiles which are suitable for masking any bitter taste from the five amino acids.

In the preferred embodiment of the food composition according to the second aspect of the present invention the food composition consists essentially of water and the food supplement according to the first aspect of the present invention.

This is especially advantageous since water is a universally accepted drink. Further as water contains essentially no proteins, fats or carbohydrates, water has a minimum impact on the body.

The term "consists essentially of" means that only those further components which do not affect the function or the effect of the food composition may be included in the food composition. Flavours, aromas, preservatives, colours, acids and bases, and the carbonisation of the water, are considered components which do not affect the function or the effect of the food composition.

Although it is still preferred that the five amino acids leucine, isoleucine, valine, threonine and lysine are the only amino acids in the food composition that are free or provided as peptides comprising at the most 10 amino acids, this is not necessary in this embodiment where there are no other amino acids than the five amino acids in the food composition.

In one embodiment of the preferred embodiment of the food composition according to the second aspect of the present invention the food composition consists of carbonated water, the food supplement according to the first aspect of the present invention, potassium sorbate and sodium benzoate, and natural pomegranate flavouring.

The third and fourth corresponding aspects of the present invention relate to the five amino acids leucine, isoleucine, valine, threonine and lysine, for use in a method of treating, controlling or preventing diseases or conditions related to the metabolic syndrome, treating or controlling diabetes, treating, controlling or preventing obesity, promoting satiety, promoting weight loss, or promoting maintenance of a healthy bodyweight, wherein 1.75 to 3.5 g of the five amino acids is administered to, or consumed by, a subject prior to, or at the same time as, the subject consumes a meal, and wherein chromium, in an amount of 4.5 to 61 µg, is also administered to, or consumed by, the subject prior to, or at the same time as the subject consumes a meal, and, a method of treating, controlling or preventing diseases or conditions related to the metabolic syndrome, treating or controlling diabetes, treating, controlling or preventing obesity, promoting satiety, promoting weight loss, or promoting maintenance of bodyweight, wherein 1.75 to 3.5 g of the five amino acids leucine, isoleucine, valine, threonine and lysine is administered to, or consumed by, a subject prior to, or at the same time as, the subject consumes a meal, and wherein chromium, in an amount of 4.5 to 61 µg, is also administered to, or consumed by, the subject prior to, or at the same time as the subject consumes a meal, respectively.

The diseases or conditions related to the metabolic syndrome comprises may be selected from the group consisting of insulin resistance, hyperinsulinemia, impaired glucose tolerance, hyperlipidemia, hypercholesterolemia, hypertension, and abdominal obesity. Diabetes is typically type 2 Diabetes Mellitus.

Treating, controlling or preventing obesity may comprise promoting satiety, promoting weight loss, and/or promoting maintenance of a healthy bodyweight.

A healthy bodyweight is specific for each subject and may for example be determined by a doctor or a dietitian. General guidelines may specify that a subject has a healthy bodyweight by measuring the subject's BMI (Body Mass Index), where for example a BMI below 30, or for example a BMI below 35, or for example a BMI below 28, may correspond to a healthy body weight, of by measuring the waist circumference where a circumference of for example below 102 cm, or for example below 94 cm, may correspond to a healthy body weight.

Obesity may be prevented, treated or controlled ultimately by the reduction of postprandial glycaemia and the thereby achieved less fluctuating blood sugar which promotes satiety. Promotion of satiety, weight loss, and maintenance of a healthy bodyweight are obtained by the reduction of postprandial glycaemia and promoted satiety.

The meal may for example be breakfast, brunch, lunch, a snack, dinner, supper, or evening meal. The meal typically comprises carbohydrates or sugars.

The subject is preferably a human being.

The amounts of the five amino acids leucine, isoleucine, valine, threonine and lysine administered or consumed may be those previously described for the five amino acids in the food supplement according to the first aspect of the present invention. Thus the five amino acids may each independently be administered or consumed in amounts from 1 to 99%, such as 1-80%, from 10-50, 10-40, 10-35, 10-25%, such as from 6-12%, 7-15%, from 5-35%, 40-60%, 50-75%, 46-37%, 3-16%, such that the sum of all present amino acids is 100% of the weight of the five amino acids administered or consumed.

In one embodiment of the third and fourth aspects of the present invention leucine is administered or consumed in an amount of 10-50%, isoleucine is administered or consumed in an amount of 5-35%, valine is administered or consumed in an amount of 10-25%, threonine is administered or consumed in an amount of 10-35% and lysine is administered or consumed in an amount of 10-25%, wherein the percentages are calculated on the sum content of the five amino acids administered or consumed and wherein the sum of the percentages of the five amino acids administered or consumed is 100%.

The five amino acids may be free or provided as peptides comprising, or consisting of, at the most 10 amino acids.

In the preferred embodiment of the third and fourth aspects of the present invention leucine, isoleucine, valine, threonine and lysine are the only amino acids administered or consumed. No further amino acids are necessary to obtain the reduction in postprandial glycaemia. This encompasses that the five amino acids leucine, isoleucine, valine, threonine and lysine should be the only amino acids administered or consumed that are free or provided as peptides comprising at the most 10 amino acids.

In another preferred embodiment of the third and fourth aspects of the present invention essentially the five amino acids leucine, isoleucine, valine, threonine and lysine are administered or consumed.

In the preferred embodiments of the third and fourth aspects of the present invention at least 0.5 g, such as at least 1.3 g, of the five amino acids is consumed by, or administered to, the subject prior to the meal. At least 4.5 µg chromium should be consumed by, or administered to, the subject prior to the meal.

0.5 g of the five amino acids corresponds to the amount consumed by the test subjects of Example 1, before the meal, at the lowest amount of the five amino acids.

The five amino acids may be administered or consumed both prior to and at the same time as the meal. Preferably a portion of the amino acids corresponding to at least 0.5 g is administered or consumed prior to the meal and the remainder of the five amino acids are consumed or administered at the same time, or during, the meal.

In the preferred embodiments of the third and fourth aspects of the present invention at least 0.5 g of the five amino acids is consumed by, or administered to, the subject within 20 minutes, such as within 1 second, such as within 30 seconds, such as within 1 minute, such as within 3 minutes, such as within 6 minutes, prior to the meal. Accordingly at least 4.5 µg chromium should be consumed, or administered to, the subject within the same times.

Without wishing to be bound by theory the present inventors nevertheless theorize that an initial consumption or administration of the five amino acids causes the body of the subject to be better prepared for the subsequent meal, thereby allowing the body time to better handle insulin secretion and glucose metabolism to thereby reduce postprandial glycaemia and postprandial insulin secretion by improving insulin economy.

Alternatively at least 0.5 g of the five amino acids may be consumed by, or administered to, the subject 1-20, such as 1-15, such as 1-10, such as 1-5, such as 1-2, such as 1-3, such as 3-5, such as 5-10, such as 5-15, such as 10-20, such as 10-15, such as 15-20, such as 1, 2, 3, 4, 5, 6, 7, 8, 9, 10, 11, 12, 13, 14, 15, 16, 17, 18, 19, or 20 minutes prior to the meal. Accordingly at least 4.5 µg chromium should be consumed, or administered to, the subject within the same times.

The five amino acids should not be consumed by, or administered to, the subject more than 20 minutes prior to the meal.

In the preferred embodiments of the third and fourth aspects of the present invention the subject is in need of controlling or preventing diseases or conditions related to the metabolic syndrome, treating or controlling diabetes, treating, controlling or preventing obesity, promoting satiety, promoting weight loss, or promoting maintenance of a healthy bodyweight.

For such a subject the third and fourth aspects of the present invention will provide at least one of the stated benefits.

However, in alternative embodiments of the third and fourth aspects of the present invention the subject is not in need of controlling or preventing diseases or conditions related to the metabolic syndrome, treating or controlling diabetes, treating, controlling or preventing obesity, promoting satiety, promoting weight loss, or promoting maintenance of a healthy bodyweight. Also this subject can benefit from the reduced postprandial glycaemia and insulin secretion as the herewith connected less fluctuating blood sugar results in a higher mental productivity.

In the preferred embodiments of the third and fourth aspects of the present invention the method of treating, controlling or preventing diseases or conditions related to the metabolic syndrome, treating or controlling diabetes, treating, controlling or preventing obesity, promoting satiety, promoting weight loss, or promoting maintenance of a healthy bodyweight, comprises lowering postprandial glycaemia, and preferably also lowering postprandial insulin secretion and/or increasing postprandial GLP-1 levels, in the subject.

In the third and fourth aspects of the present invention chromium is also administered to, or consumed by, the subject prior to, or at the same time as the subject consumes a meal.

As shown in the examples and as shown by WO2012177215, chromium plays a role in limiting postprandial glycaemia and insulin secretion.

In the preferred embodiments of the third and fourth aspects of the present invention the five amino acids are administered to, or consumed by, the subject as the food supplement according to the first aspect of the present invention or as the food composition according to the second aspect of the present invention.

A further aspect of the present invention relates to the food supplement according to the first aspect of the present invention or the food composition according to the second aspect of the present invention for use according to the third aspect of the present invention or in the method according to the fourth aspect of the present invention.

Example 1—Composite Meal Challenge Study 1.1. Material and Methods

The composite meal challenge study included: 125 g of frozen fillet of cod, cooked without added water in a covered bowl in a microwave oven (3.5 min, 800 W); 250 g mashed potatoes, made from reconstituted potato powder containing 99% dried potato (ICA Basic Potatismos, ICA AB, Solna, Sweden); 50 g lingonberry jam (Lingonsylt, ICA AB, Solna, Sweden); 20 g melted butter (Smör Normalsaltat, Skånemejerier, Malmö, Sweden) and 50 g fresh cucumber.

Test and Reference Drinks

The composite meal was provided with 330 mL of carbonated water to which different concentrations of 5AA+CrPic was added. The different test meals were named after the concentration (high, medium or low) of 5AA+CrPic added to the drink; 5AACr-high, and 5AACr-low (detailed recipes in Table 1 below).

TABLE 1

Concentrations of 5AA + CrPic in the different test drinks

| Drink | 5AA (g/330 mL serving) | CrPic (µg/330 mL serving) |
| --- | --- | --- |
| Ref | 0 | 0 |
| 5AACr-high | 6.9 | 500 |
| 5AACr-med | 3.5 | 250 |
| 5AACr-low | 1.75 | 125 |

The composite meal served with a reference drink without addition of 5AA+CrPic was named Ref. The carbonated waters were provided by EW Flavours (Malmö, Sweden) and all waters, including the Ref, had a synthetic Lemon-Lime flavour. The total macronutrient composition of the different meals including the drinks can be seen in Table 2.

TABLE 2

Total macronutrient composition of the different test meals, including the drinks, basedon information in food database (Swedish National Food Agency, 2012) and from manufacturers.

| | | Meal | | | |
| --- | --- | --- | --- | --- | --- |
| | | 5AACr-high | 5AACr-med | 5AACr-low | Ref |
| Carbohydrates | g | 50.1 | 50.1 | 50.1 | 50.1 |
| of which monosaccharides | g | 20 | 20 | 20 | 20 |
| Fat | g | 17.3 | 17.3 | 17.3 | 17.3 |
| Protein | g | 33.6 | 30.1 | 28.4 | 26.7 |
| Energy | Kcal | 500 | 486 | 479 | 472 |

The subjects were instructed to drink a 100 mL portion of the water within three minutes before starting the meal and the remaining 230 mL was taken along with the food.

1.2. Test Subjects and Study Design 16 healthy non-smoking subjects (7F, 9M) aged 37-66 y (54±6 y; mean±s) with a body mass index (BMI; in kg/m2) between 23-32 (27.5±2.4; mean±s) participated in the study. All subjects had normal fasting blood glucose levels (5.5±0.5 mmol/L; mean±s). Two subjects stated that they medicated regularly. The medications were Enalapril (hypotensive), Behepan (vitamin B12 supplement) and Loratadin (prescription-free antihistamine) These were not assumed to affect the postprandial metabolism and were therefore allowed. The subjects were asked not to take their medication in the mornings before the study visits, and otherwise maintain a constant intake over the course of the study.

The study was a randomised crossover trial; the subjects were blinded to the test products. The test meals were served as breakfast after an overnight fast at 4 different occasions, about 1 wk apart. In the evening before each study visit, the subjects were instructed to eat a standardized, low-fibre dinner of their own choice around 6 pm. Thereafter they were instructed to eat an evening meal of white wheat bread (Dollarfranska, Lockarps, Lockarp, Sweden), with sandwich spread and a drink of their own choice between 9 and 10 pm. After this meal they were to ingest nothing more than maximum half a glass of water until they were served breakfast at the laboratory. They were instructed to eat the same dinner and white wheat bread meal before all test occasions. They were also instructed not to perform any hard physical exercise or consume alcohol and to avoid foods high in fibre the day before their visits. Upon arrival at the laboratory in the morning, a peripheral catheter was inserted in an antecubital vein and a fasting blood sample was drawn. Thereafter the test meal was served. The subjects had to finish their meal within 10-14 minutes and they should alternate between eating and drinking. All meals were well tolerated by the subjects and they had no problem finishing their meal within the 14 minutes.

All of the subjects volunteered to participate in the study and gave their informed consent. The subjects were aware that they could withdraw from the study at any time, should they wish to do so. The study was approved by the Regional Ethical Board at Lund University (Dnr 2010/499).

1.3. Blood Analyses

Blood was sampled at fasting (allocated to time 0) and 15, 30, 45, 60, 90, 120 and 180 minutes after starting breakfast. Time 0 was defined as the minute when the subjects started eating the breakfast (3 minutes after having the pre-meal sip). Venous blood samples for serum insulin analysis were taken at all time points using serum separation tubes. The samples were left at room temperature for 30 minutes prior to centrifugation for 10 min (2246×g, 4° C.). Venous blood samples for GLP-1 analysis were taken during the first hour (time points 0 to 60) and collected in plasma (EDTA) tubes to which DPP-IV inhibitor (Merck Millipore, Billerica, MA, USA) had been added. The samples were kept on ice for maximum 15 min after sampling, until centrifugation for 10 min (1000×g, 4° C.). Separated serum and plasma samples were stored frozen (−20° C.) until analysis. Capillary blood glucose was measured at all time points immediately after sampling using a B-glucose analyser (Hemocue, Ängelholm, Sweden). Serum insulin was analysed using an ELISA kit (Mercodia insulin ELISA, Mercodia AB, Uppsala, Sweden), the analysis procedure was semi-automated using an ELISA robot (CODA Automated EIA Analyzer, Bio-Rad Laboratories AB, Sundbyberg, Sweden). Plasma GLP-1 was analysed manually using an ELISA kit (GLP-1 (Active 7-36) ELISA, Alpco, Salem, NH, USA).

1.4. Calculations and Statistical Methods

One subject fainted at one occasion due to discomfort when inserting the peripheral catheter. The results for this person with the test meal of that occasion (5AACr-med) had to be excluded from all calculations. The incremental area under curve (iAUC) was calculated for glucose, insulin and GLP-1 according to the trapezoidal method, excluding areas below the fasting level. The assumption that there was no significant difference between the fasting values of glucose and insulin for the different meals was verified using analysis of variance (ANOVA), general linear model, in Minitab (release 16, Minitab Inc., State Collage, PA, USA). This assumption for the GLP-1 fasting values could not be verified in the same way because they were not normally distributed. Incremental peaks (iPeaks) for glucose and insulin were calculated using GraphPad (GraphPad Prism 5, version 5.04, GraphPad Software, Inc., San Diego, CA, USA). The individual iPeak was defined as the maximum increase from baseline over the entire test duration (Rosen, Silva et al. 2009). The Mean Peak was calculated for glucose and insulin and defined as the increase from baseline for each subject and meal at the time point where most of the mean curves peaked (i.e. at 45 min for both glucose and insulin).

Glycaemic profile, GP, was calculated for the glucose response and defined as duration divided by the iPeak (Rosen, Silva et al. 2009). The duration was determined using GraphPad and defined as the time in minutes from zero to where the curve first crossed the baseline. If the curve did not reach baseline after 180 minutes, the duration was set to 180 minutes.

All values are expressed as mean±SEM, calculated with Minitab. Statistical analysis of the data was executed using a general linear model ANOVA, using subject as a random variable, followed by Tukey's multiple comparisons test in Minitab. Sixteen subjects participated in the study and four different meals were investigated. When the data was not normally distributed (according to a Normal Probability plot), it was transformed using a Box-Cox plot prior to ANOVA.

Time×treatment interactions for glucose, insulin and GLP-1 were analysed using a mixed model (PROC MIXED in SAS 9.3, SAS Institute Inc., Cary, NC, USA) with repeated measures and an autoregressive covariance structure.

1.5. Results

1.5.1. Blood Glucose Responses

Figure 1:
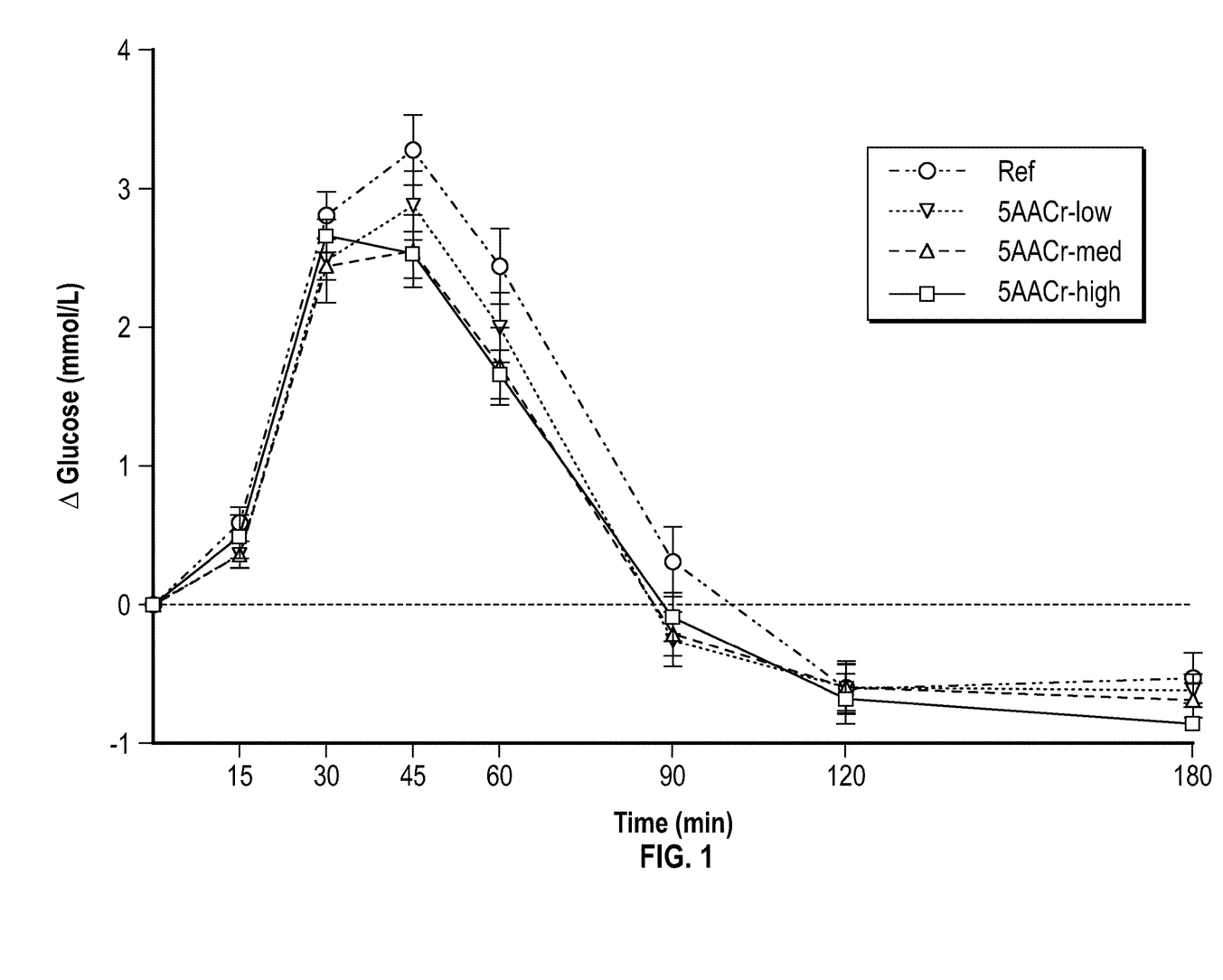
FIG. 1 shows the mean (±SEM) postprandial incremental changes (Δ) in blood glucose in response to the different test and reference meals; n=16 (n=15 for 5AACr-med)

The postprandial blood glucose responses are presented in FIG. 1, and Table 3 and 4 below:

TABLE 3

Incremental areas under the curve (iAUC) for blood glucose responses[1]

| Meal | iAUC (0-120 min) mmol · min/L | Δ % | iAUC (0-180 min) mmol · min/L | Δ % |
|---|---|---|---|---|
| Ref | 168.1 ± 16.1[a] | — | 171.0 ± 17.2[a] | — |
| 5AACr-high | 126.8 ± 6.8[b] | −25 | 128.3 ± 6.9[b] | −25 |
| 5AACr-med | 120.7 ± 1.0[b] | −28 | 122.1 ± 10.9[b] | −29 |
| 5AACr-low | 133.0 ± 12.5[b] | −21 | 134.4 ± 12.5[b] | −21 |

[1]iAUCs are given as mean ± SEM; n = 16 (n = 15 for 5AACr-med). Values in the same column with different superscript letters are significantly different, P < 0.05 (ANOVA followed by Tukey's multiple comparisons test). A change (%) calculated for the mean values.

TABLE 4

Postprandial blood glucose and serum insulin responses[1]

| Meal | Glucose iPeak Δ mmol/L | Mean Peak Δ mmol/L | Insulin iPeak Δ nmol/L | Mean Peak Δ nmol/L |
|---|---|---|---|---|
| Ref | 3.61 ± 0.18[a] | 3.28 ± 0.26[a] | 0.343 ± 0.050[a] | 0.309 ± 0.051[a] |
| 5AACr-high | 2.88 ± 0.13[b] | 2.53 ± 0.16[b] | 0.418 ± 0.052[b] | 0.382 ± 0.053[b] |
| 5AACr-med | 2.91 ± 0.19[b] | 2.55 ± 0.26[a,b] | 0.361 ± 0.059[a,b] | 0.329 ± 0.060[a,b] |
| 5AACr-low | 3.08 ± 0.21[a,b] | 2.88 ± 0.25[a,b] | 0.359 ± 0.051[a] | 0.327 ± 0.052[a,b] |

[1]All values are given as mean ± SEM; n = 16 (n = 15 for 5AACr-med). Values in the same column with different superscript letters are significantly different, P < 0.05 (ANOVA followed by Tukey's multiple comparisons test). iPeak, incremental Peak; Mean Peak, value at the time point where the mean curve peaks All test meals containing 5AA and CrPic resulted in significantly lowered blood glucose response compared to Ref, as measured by iAUC 0-120 and 0-180 min. A significant treatment effect was found (p=0.0160), but there was no time×treatment interaction (p=0.5272). Furthermore, the 5AACr-high and 5AACr-med meals resulted in significantly lowered glucose iPeaks (Δmmol/L) compared to Ref. The 5AACr-high also gave a significantly lowered Mean Peak for glucose (Δmmol/L). There were no differences in glycaemic profile (GP, mmol·min/L) between any of the test meals.

1.5.2. Serum Insulin Responses

Figure 2:
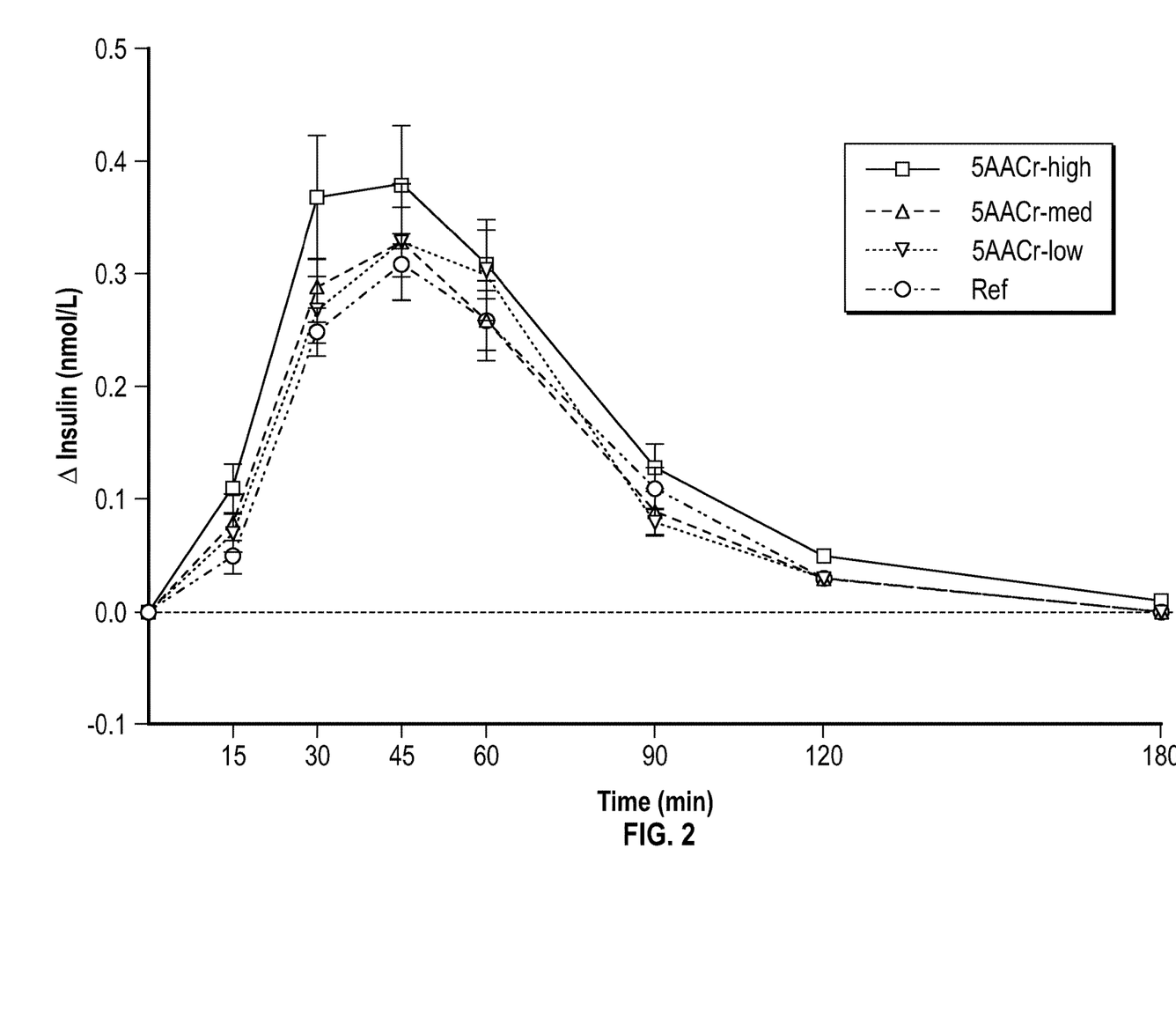
FIG. 2 shows the mean (±SEM) postprandial incremental changes (Δ) in serum insulin in response to composite meal served with different test and reference drinks; n=16 (n=15 for 5AACr-med)

The postprandial insulin responses are presented in FIG. 2, Table 4 above and Table 5 below:

TABLE 5

Incremental areas under the curve (iAUC) for serum insulin responses[1]

| Meal | iAUC (0-15 min)[2] nmol · min/L | Δ % | iAUC (0-30 min)[2] nmol.min/L | Δ % | iAUC (0-120 min) nmol · min/L | Δ % | iAUC (0-180 min) nmol · min/L | Δ % |
|---|---|---|---|---|---|---|---|---|
| Ref | 0.41 ± 0.12[a] | — | 2.65 ± 0.56[a] | — | 18.69 ± 2.25[a] | — | 19.62 ± 2.29[a] | — |
| 5AACr-high | 0.80 ± 0.16[b] | +94 | 4.40 ± 0.69[b] | +66 | 24.71 ± 2.79[b] | +32 | 26.52 ± 2.84[b] | +35 |
| 5AACr-med | 0.57 ± 0.19[a,b] | +39 | 3.29 ± 0.81[a] | +24 | 19.40 ± 2.83[a] | +4 | 20.32 ± 2.84[a] | +4 |
| 5AACr-low | 0.50 ± 0.13[a] | +20 | 3.00 ± 0.48[a] | +13 | 19.30 ± 2.70[a] | +3 | 20.17 ± 2.71[a] | +3 |

[1]iAUCs are given as mean ± SEM; n = 16 (n = 15 for 5AACr-med).
Values in the same column with different superscript letters are significantly different, P < 0.05 (ANOVA followed by Tukey's multiple comparisons test).
Δ change (%) calculated for the mean values.
[2]Residuals were not normally distributed and Box-Cox transformation was performed on the data prior to ANOVA.
Untransformed mean values are shown.

The meal supplemented with 5AACr-high resulted in significantly higher serum insulin responses than Ref, both in the early (iAUC 0-30 min) and overall (iAUC 0-180 min) postprandial phase. The insulin iPeak (ΔmmoL/L) as well as the Mean Peak (ΔmmoL/L) were significantly higher for 5AACr-high compared to Ref. The insulin responses following the 5AACr-med and 5AACr-low, respectively, could not be distinguished from Ref meal with water. There was a tendency towards a treatment effect (p=0.0553) but no time×treatment interaction (p=0.7557).

Figure 4:
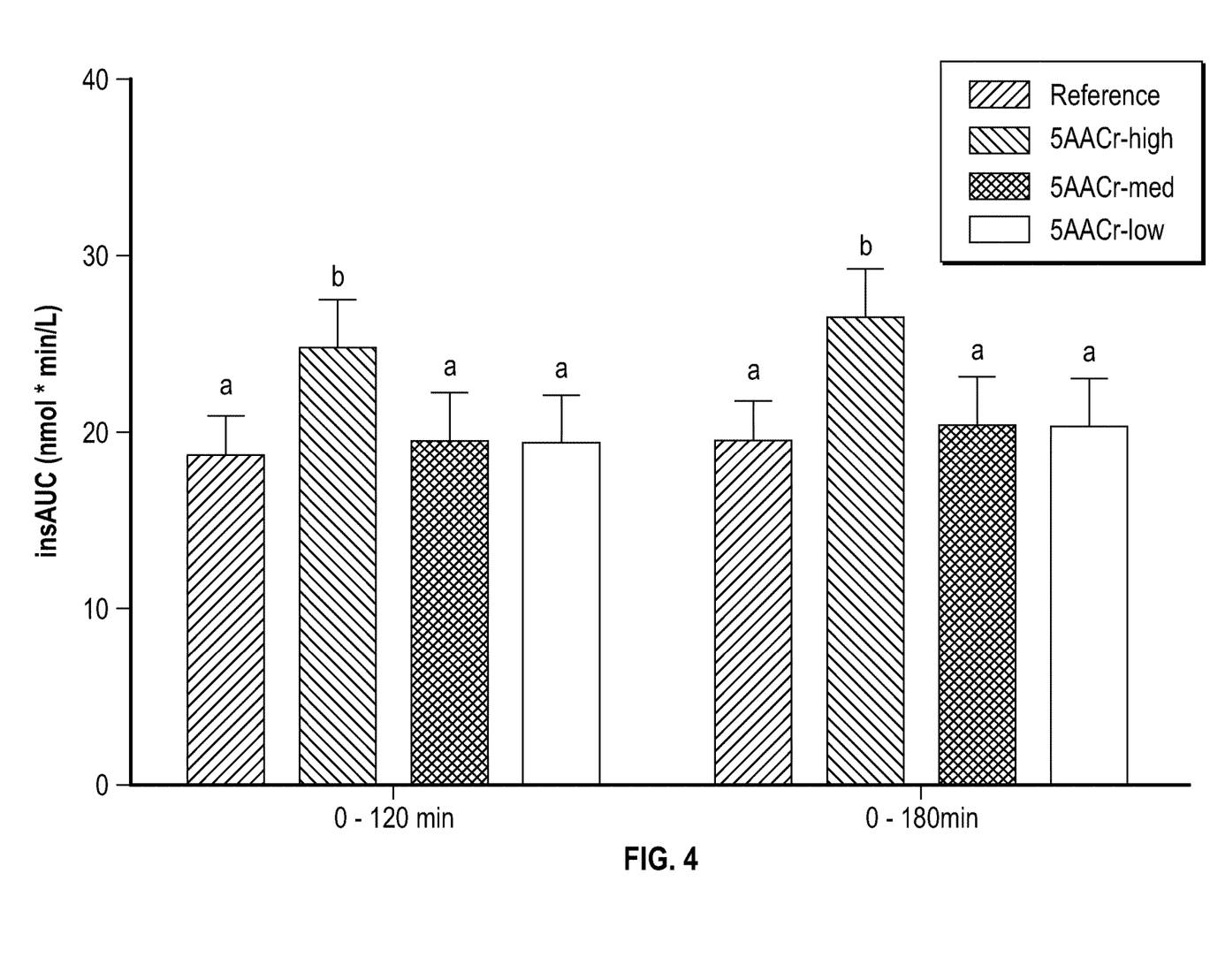
FIG. 4 shows a comparison of overall insulin responses at 2 and 3h, respectively after intake of a composite meal served with different test and reference drinks; n=16 (n=15 for 5AACr-med at all time points and for 5AACr-high and 5AACr-low at 60 min)

Thus the present experiments shows that carbonized table water containing CrPic (125-500 μg/serving) and 5AA (1.75-6.9 g/serving) could improve postprandial glycaemia after intake of a challenging composite meal consisting of cod fillet and mashed potatoes. In fact, the overall glucose responses were significantly lowered by more than 20% compared to Ref with all three doses of 5AA+CrPic. The insulin response after intake of 5AACr-high was significantly higher compared to Ref. However, the present example shows that 5AACr-med and 5AACr-low did not significantly increase the overall insulin response to the composite cod/potato meal. Yet the two lower doses (5AACr-med and 5AACr-low) lowered postprandial glycaemia to a similar extent as with 5AACr-high, indicating an improved insulin economy. A summary of insulinaemic responses (incremental AUC 0-120 min) after the Ref meal with water or Ref meal supplemented with the three different levels of CrPic+5AA, respectively, is displayed in FIG. 4.

In the present experiment, all three doses of the 5AA+CrPic mixture significantly increased early insulin responses (0-15 min), which appeared to be important for the overall benefits on postprandial blood glucose regulation.

In contrast to prior art experiments the subjects were instructed to consume most of the drinks (⅔) during the course of the meal, and ⅓ immediately before the meal, more mimicking normal eating behaviour. Given in this fashion, the test drinks exhibited positive effects on blood glucose regulation compared with the Ref meal with water. At the low and medium levels of 5AA+CrPic, this was achieved in the absence of an increase in overall insulin response compared with the ref meal.

The highest level of AA in the present example is equivalent to the contribution of these AA from approximately 600 ml milk. A regular consumption of the table water containing the 5AA+CrPic mix at the 2 lower doses, together with all the three main meals of the day, would correspond to an increase in protein intake of about 5 to 10 g (1.7 and 3.4 g protein, respectively, per serving of 5AACr-low and 5AACr-med). This would increase daily energy intake with 20 to 40 kcal, which represents about 1 to 2 E % of a total energy intake corresponding to 2000 kcal/day. This extra intake of protein should be well within the frames of a generally acceptable healthy dietary regimen.

1.5.3. Plasma GLP-1 Responses

Figure 3:
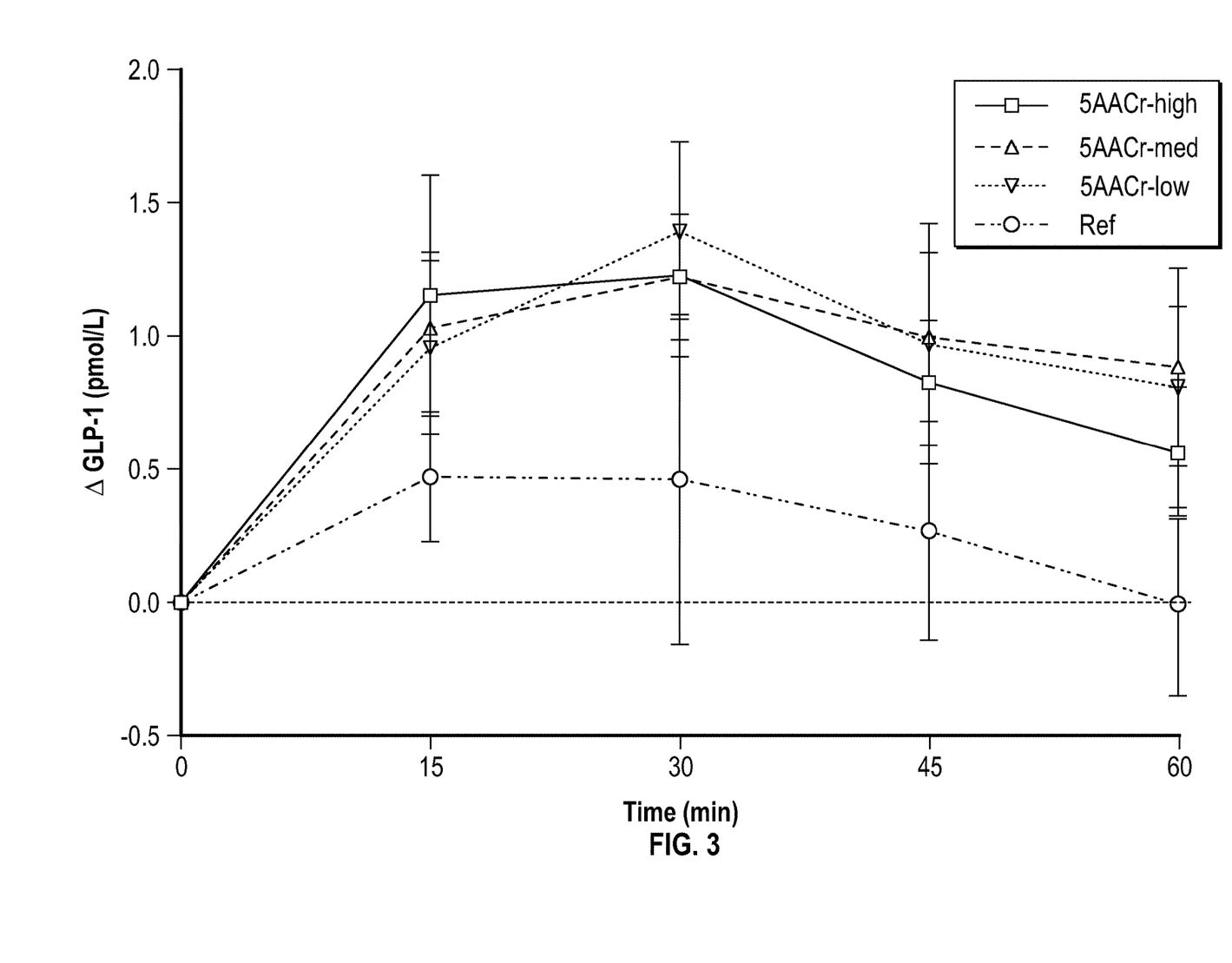
FIG. 3 shows the mean (±SEM) postprandial incremental changes (Δ) in plasma GLP-1 in response to composite meal served with different test and reference drinks; n=16 (n=15 for 5AACr-med at all time points and for 5AACr-high and 5AACr-low at 60 min)

The postprandial GLP-1 responses are presented in FIG. 3 and Table 6 below:

TABLE 6

Incremental areas under the curve (iAUC) for plasma GLP-1 responses[1]

| Meal | iAUC (0-60 min)[2] pmol · min/L | Δ % |
|---|---|---|
| Ref | 37.5 ± 6.9[a] | — |
| 5AACr-high | 52.0 ± 13.7[a] | +39 |
| 5AACr-med | 58.0 ± 12.7[a] | +55 |
| 5AACr-low | 61.9 ± 15.5[a] | +65 |

TABLE 6-continued

Incremental areas under the curve (iAUC) for plasma GLP-1 responses[1]

| Meal | iAUC (0-60 min)[2] pmol · min/L | Δ % |
|---|---|---|

[1]iAUCs are given as mean ± SEM; n = 16 for Ref and n = 15 for 5AACr-high, 5AACr-med and 5AACr-low. Values in the same column with different superscript letters are significantly different, P < 0.05 (ANOVA followed by Tukey's multiple comparisons test). A change (%) calculated for the mean values.
[2]Residuals were not normally distributed and Box-Cox transformation was performed on the data prior to ANOVA. Untransformed mean values are shown.

There was a trend towards higher GLP-1 responses, i.e. higher GLP-1 levels, after all three test meals including 5AA and CrPic drink compared with Ref. However, the differences were not significant. There was no significant treatment effect (p=0.1327) nor time×treatment interaction (p=0.9303).

Example—2 Table Water

A prototype table water was further developed based on the 5AACr-med drink. In addition to carbonated water, 3.5 g of the five amino acids and 250 μg chromium piccolinate, the prototype table water contained preservatives (potassium sorbate and sodium benzoate) and natural pomegranate flavouring. The energy content of the prototype table water is 4 kcal per 100 ml. The prototype table water has the appearance and taste of conventional flavoured carbonated table waters. With the natural pomegranate flavouring no bitter taste from the five amino acids could be detected by test persons.

Example 3—Standardized Sandwich Breakfast Study

A further study was made with two additional levels of the five amino acids leucine, isoleucine, valine, lysine and threonine, the levels being 2.6 g and 5.2 g per dose/serving.
3.1. Subjects and Methods The study was of randomized, double blind, within subject design. 9 men and 10 women completed the study. The study subjects had a mean BMI of 24.1 kg/m$^2$, the values ranging between 18.5 and 31.9. The mean age of the subjects was 26.2 years, the values ranging between 21-43. None of the subjects had a metabolic disease.

The standardized sandwich breakfast consisted of white wheat bread with butter and strawberry jam corresponding to 50 g available carbohydrates.

The standardized breakfast sandwich was served with 330 ml carbonated and lightly flavoured water (Control), or the same water containing 2.6 g or 5.2 of the five amino acids leucine, isoleucine, valine, lysine and threonine and 250 μg CrPic), (2.6AA+CrPic and 5.2AA+CrPic, respectively).

Half of the water volume was ingested during the 6 min before starting eating the sandwich, and the rest of the water was ingested while eating the sandwiches.

Glucose and insulin responses were measured in venous blood at −6 (fasting), 15, 30, 60, 90, 120 and 180 min after starting the meal.

Glucose and insulin responses were measured as described in Example 1, section 1.3 above, and the results analyzed statistically as described in Example 1, section 1.4 above.

As half of the water volume was ingested during the 6 min before starting eating the sandwich, the subjects ingested 1.3 g, and 2.6 g, respectively, of the five amino acids during this interval.

3.2. Results

Figure 5A:
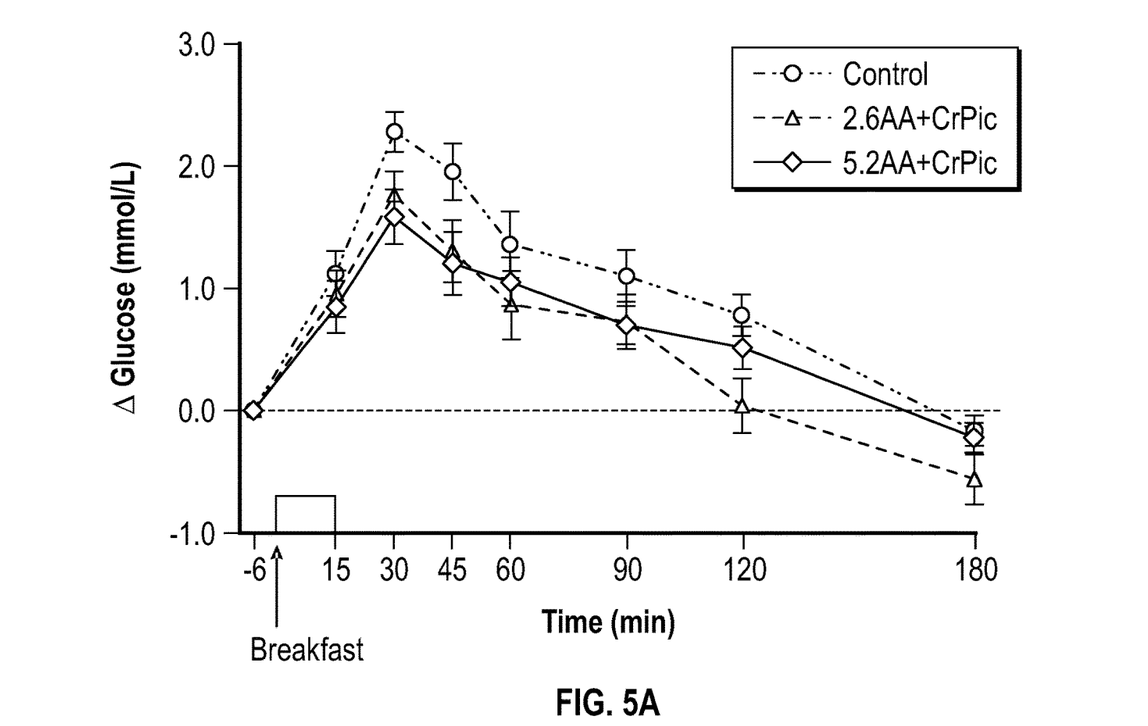
FIGS. 5A and 5B show the mean (±SEM) postprandial incremental changes (Δ) in blood glucose (FIG. 5A), and the area under the curve (AUC) (FIG. 5B) for blood glucose in response to a standardized sandwich breakfast served with different test drinks.

FIG. 5A shows the mean (±SEM) postprandial incremental changes (Δ) in blood glucose for the Control, the 2.6AA+CrPic, and the 5.2AA+CrPic—drinks. As is seen in the graph the incremental change in blood glucose for the water with amino acids and CrPic, i.e. for 2.6AA+CrPic and 5.2AA+CrPic, is lower for all time points than Control. 5.2AA+CrPic gives the lowest change in blood glucose for the time interval −6 to 45 minutes, while 2.6AA+CrPic provides the lowest change in blood glucose for the time interval 60-180 minutes.

Figure 5B:
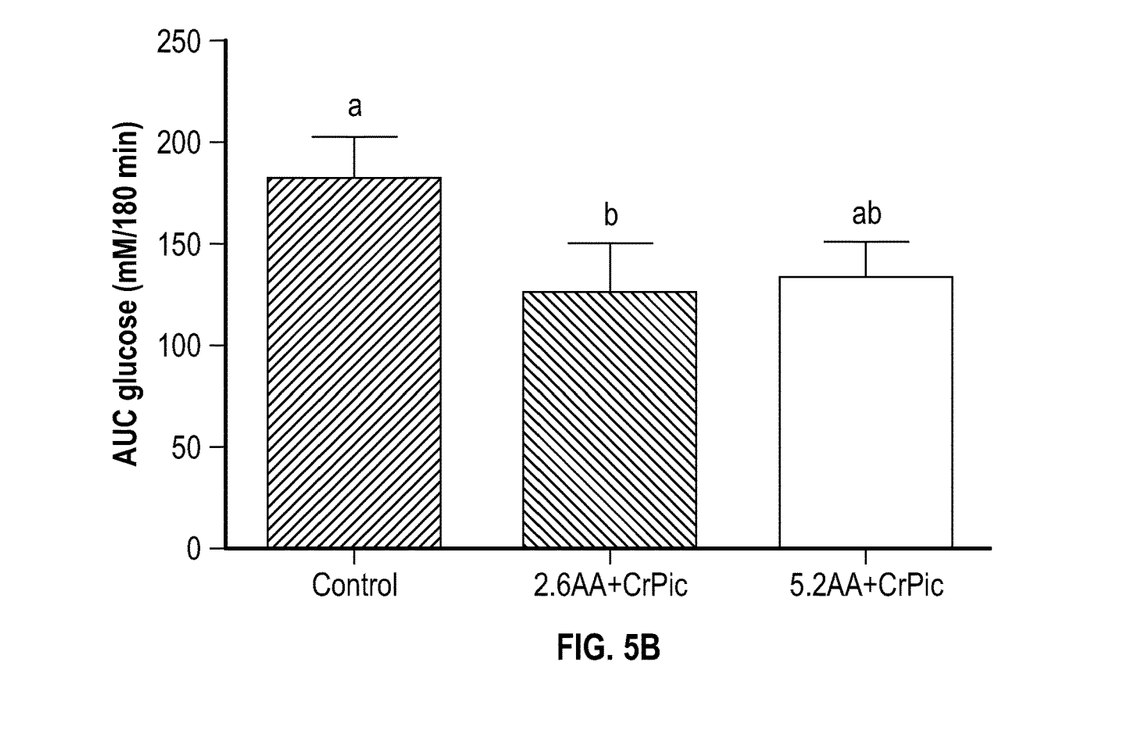

The different incremental changes in blood glucose also influence the area under the curve (AUC) for the blood glucose responses in FIG. 5A. As shown in FIG. 5B, 2.6AA+CrPic provides a significantly (as indicated by the different letters "a" and "b" assigned to the bars in the chart) lower AUC value than the Control. 5.2AA+CrPic also provides a lower AUC value than control, however this value is not significantly different from that of Control and 2.6AA+CrPic. The AUC-values in FIG. 5B are calculated on the full time period of the meal, i.e. from 0 to 180 minutes.

Figure 6A:
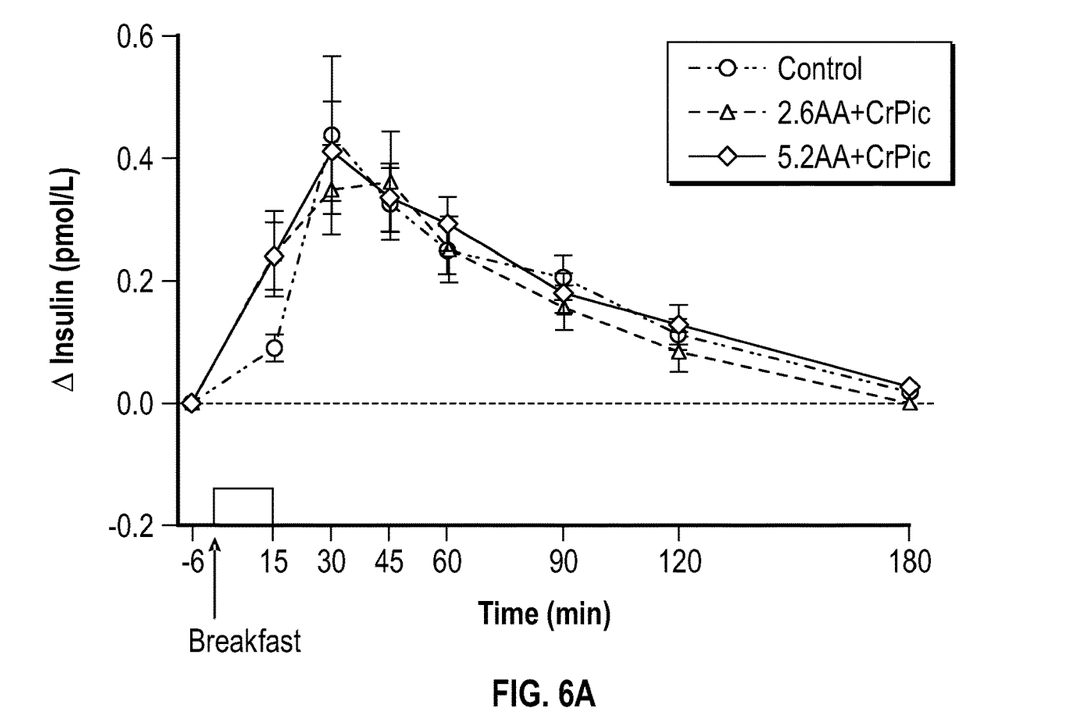
FIGS. 6A and 6B show the mean (±SEM) postprandial incremental changes (Δ) (FIG. 6A) in serum insulin, and the area under the curve (AUC) (FIG. 6B) for insulin, in response to a standardized sandwich breakfast served with different test drinks.

FIG. 6A shows the mean (±SEM) postprandial incremental changes (Δ) in serum insulin, for the Control, the 2.6AA+CrPic, and the 5.2AA+CrPic—drinks. As is seen in the graph the incremental change in serum insulin for 2.6AA+CrPic and 5.2AA+CrPic follows the values for the Control closely, except for the time interval −6 to 30 minutes. Generally, 2.6AA+CrPic gives the lowest change in serum insulin for the time interval to 180 minutes, lower even than the Control.

Figure 6B:
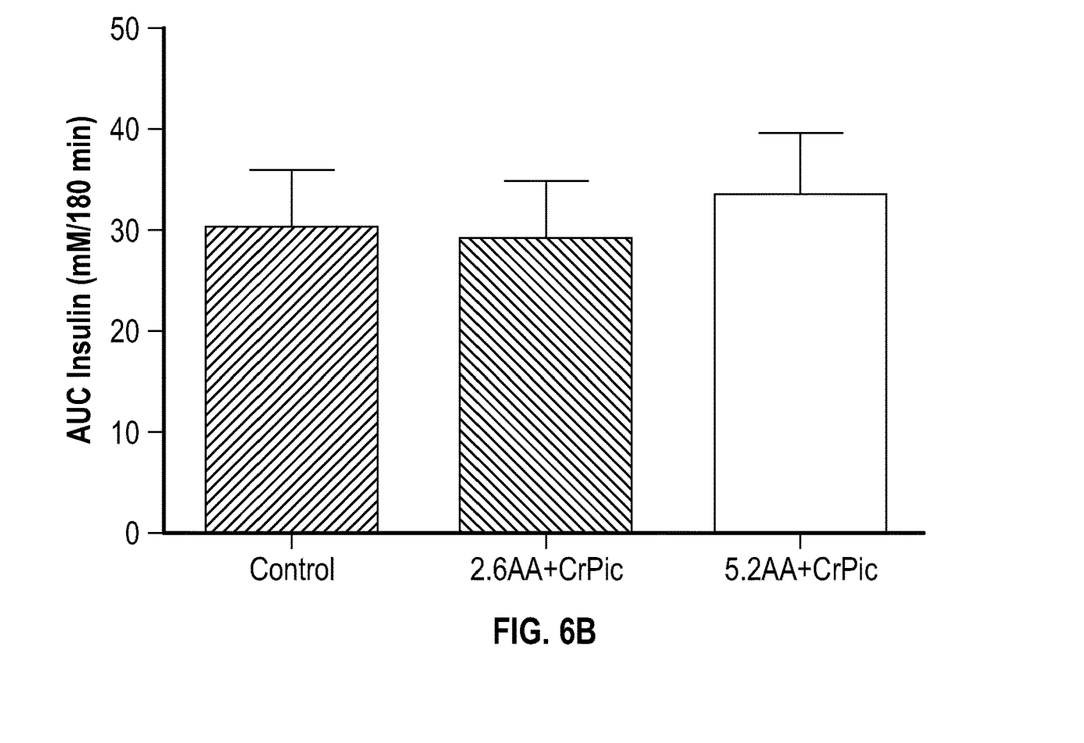

The different incremental changes in serum insulin also influence the area under the curve (AUC) for the serum insulin responses in FIG. 6A. As shown in FIG. 6B, 2.6AA+CrPic provides an AUC value lower even than the Control. 5.2AA+CrPic on the other hand provides a slightly higher AUC value, however none of the AUC values differ significantly from the others. This is important in that it shows that the 2.6AA+CrPic and 5.2AA+CrPic provide lower incremental change in blood glucose without increasing insulinemia. Accordingly the 2.6AA+CrPic significantly reduced postprandial glycaemia caused by the consumption of the standardized sandwich meal with as much as 30% (as shown in FIG. 5B), without significantly increasing insulinemia (as shown in FIG. 6B) when compared to the Control. 5.2AA+CrPic did not significantly reduce postprandial glycaemia for the full 180 minutes.

Example 4—Study of Lower Doses on Sandwich Meal

A further study was made comparing the postprandial glucose lowering potential of two lower doses of the five amino acids leucine, isoleucine, valine, lysine and threonine, these lower doses being 1.3 and 0.65 g, the postprandial glucose lowering potential of the previously studied dose of 2.6 g.

4.1. Subjects and Methods

The study was of randomized, double-blind, within-subject design. 12 men and 13 women were included in the study. The subjects had a mean BMI of 22.8 kg/m², the values ranging between 19 and 25. The mean age was 26.7 years with values ranging between 19 and 52. None of the subjects had any metabolic disease.

The meal was a standardized sandwich breakfast consisting of white wheat bread with butter and ham, corresponding to 50 g of available carbohydrates.

The meal was served with 330 mL carbonated and lightly flavored water (Control) or the same water containing 0.65, 1.3 or 2.6 g of the amino acids leucine, isoleucine, valine, lysine and threonine. All drinks (except Control) contained 250 mcg CrPic.

⅓ of the water volume was taken during 3 min before starting the breakfast meal and the rest while eating the sandwiches.

Capillary blood for glucose analysis and venous blood for insulin responses were collected at −3 (fasting), 15, 30, 45, 60, 90, 120 and 180 min after the start of the sandwich meal.

Glucose and insulin responses were measured as described in Example 1, section 1.3 above, and the results analyzed statistically as described in Example 1, section 1.4 above.

As ⅓ of the water volume was ingested during the 3 min before starting eating the sandwich, the subjects ingested 0.22 g, 0.43 g, and 0.87 g, respectively, of the five amino acids before starting the sandwich meal.

4.2. Results

The results from a sub-group of 11 subjects are shown in Table 7. They show that the best glucose lowering is obtained by the 2.6 g AA-level and that the two lower AA-levels do not reduce glycaemia compared to Control.

TABLE 7

Incremental areas under the curve (iAUC) for blood glucose responses

| Test meal | iAUC 0-180 min (mean ± SEM) | N |
|---|---|---|
| Control (without AA and CrPic) | 127.3 ± 25.1$^{ab}$ | 10 |
| 0.65 g AA + 250 mcg CrPic | 143.1 ± 21.8$^{ab}$ | 11 |
| 1.3 g AA + 250 mcg CrPic | 179.8 ± 18.8$^{a}$ | 11 |
| 2.6 g AA + 250 mcg CrPic | 97.4 ± 12.2$^{b}$ | 11 |

Rows not sharing the same superscript letter are significantly different

In summary of the results obtained in examples 1–4 above it appears that an amount/dose of the five amino acids between 1.75 and 3.5 g, such as in particular 2.6 g, provides the best effect in lowering postprandial glycaemia without increasing postprandial insulinemia.

A further exemplary conceptual embodiment concerns a food supplement comprising the five amino acids leucine, isoleucine, valine, threonine and lysine, wherein the sum content of the five amino acids is less than 6.9 g. The sum content of the five amino acids may for example be at least 0.5 g. Preferably the sum content of the five amino acids is from 1.75 to 3.5 g. Leucine may be present in an amount of 10-50%, isoleucine in an amount of 5-35%, valine in an amount of 10-25%, threonine in an amount of 10-% and lysine is present in an amount of 10-25%, wherein the percentages are calculated on the sum content of the five amino acids in the food supplement and wherein the sum of the percentages of the five amino acids in the food supplement is 100%. Leucine, isoleucine, valine, threonine and lysine are preferably the only amino acids present in the food supplement. Preferably the food supplement further comprises chromium.

A further exemplary conceptual embodiment concerns a food composition comprising the food supplement. The food composition may be in an amount suitable for being consumed prior to, or together with, a meal. The food composition may be a beverage such as water, tea, malt beverages, coffee, soft drinks, juice, yoghurt, milk, soymilk or oatmilk. The food composition may consist essentially of water and the food supplement.

A further exemplary conceptual embodiment concerns the five amino acids leucine, isoleucine, valine, threonine and lysine, for use in a method of treating, controlling or preventing diseases or conditions related to the metabolic syndrome, treating or controlling diabetes, treating, controlling or preventing obesity, promoting satiety, promoting weight loss, or promoting maintenance of a healthy bodyweight, wherein less than 6.9 g of the five amino acids is administered to, or consumed by, a subject prior to, or at the same time as, the subject consumes a meal. At least 0.5 g of the five amino acids may be consumed by, or administered to, the subject within 20 minutes, such as within 1 second, such as within 30 seconds, such as within 1 minute, such as within 3 minutes, prior to the meal. The method of treating, controlling or preventing diseases or conditions related to the metabolic syndrome, treating or controlling diabetes, treating, controlling or preventing obesity, promoting satiety, promoting weight loss, or promoting maintenance of a healthy bodyweight, may comprise lowering postprandial glycaemia, and preferably also lowering postprandial insulin secretion and/or increasing postprandial GLP-1 levels, in the subject. Chromium may also be administered to, or consumed by, the subject prior to, or at the same time as the subject consumes a meal. The five amino acids may be administered to, or consumed by, the subject as the food supplement or as the food composition.

REFERENCES

Rosen, L. A. H., L. O. B. Silva, et al. (2009). "Endosperm and whole grain rye breads are characterized by low post-prandial insulin response and a beneficial blood glucose profile." Nutrition Journal 8(42): (25 Sep. 2009).

The invention claimed is:

1. A method comprising a dose of a food supplement being consumed by, administered to, a subject prior to or at the same time as the subject consumes a meal, the dose of the food supplement comprising chromium and the five amino acids leucine, isoleucine, valine, threonine and lysine, wherein leucine, isoleucine, valine, threonine and lysine are the only amino acids present in the dose of the food supplement, and wherein the sum content of the five amino acids is from 1.75 to 3.5 g in the dose of the food supplement, and wherein the content of chromium is from 4.5 to 61 µg in the dose of the food supplement.

2. The method according to claim 1, wherein the sum content of the five amino acids is from 1.75 to 2.6 g, or from 2.6 to 3.5 g, in the dose of the food supplement.

3. The method according to claim 1, wherein the content of chromium is from 4.5 to 31.1 µg, such as 15.5 to 31.1 µg, per in the dose of the food supplement.

4. The method according to claim 1, wherein, in the dose of the food supplement, leucine is present in an amount of 10-50%, isoleucine is present in an amount of 5-35%, valine is present in an amount of 10-25%, threonine is present in an amount of 10-35% and lysine is present in an amount of 10-25%, wherein the percentages are calculated on the sum content of the five amino acids in the dose of the food supplement and wherein the sum of the percentages of the five amino acids in the dose of the food supplement is 100%.

5. The method according to claim 1, wherein the sum content of the five amino acids is 2.6 g in the dose of the food supplement.

6. The method according to claim 5, wherein the content of chromium is 31.1 µg in the dose of the food supplement.

7. The method of claim 1 wherein the dose of the food supplement is formulated as a food composition, wherein the five amino acids leucine, isoleucine, valine, threonine and lysine are the only amino acids in the food composition that are free or provided as peptides comprising at the most 10 amino acids.

8. The method according to claim 7, wherein the dose of the food supplement is formulated as a beverage selected from the group consisting of water, tea, malt beverages, coffee, soft drinks, juice, yoghurt, milk, soymilk and oatmilk.

9. The method according claim 7, wherein the dose of the food supplement is formulated in.

10. The method of claim 1, wherein the dose of the food supplement, is consumed by, or administered to, the subject within 20 minutes, such as within 1 second, such as within 30 seconds, such as within 1 minute, such as within 3 minutes, such as within 6 minutes, prior to the meal.

11. The method of claim 1, wherein the subject has a metabolic syndrome, diabetes, or obesity.

* * * * *